US010149893B2

(12) United States Patent
Jiang et al.

(10) Patent No.: US 10,149,893 B2
(45) Date of Patent: Dec. 11, 2018

(54) METHODS FOR MODIFYING PROGRESSION OF OSTEOARTHRITIS

(71) Applicant: Allergan, Inc., Irvine, CA (US)

(72) Inventors: Guang L. Jiang, Irvine, CA (US); Catherine Turkel, Newport Coast, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/035,622

(22) Filed: Sep. 24, 2013

(65) Prior Publication Data
US 2015/0086531 A1 Mar. 26, 2015

(51) Int. Cl.
*A61K 38/48* (2006.01)
*A61K 9/00* (2006.01)

(52) U.S. Cl.
CPC ........ *A61K 38/4893* (2013.01); *A61K 9/0019* (2013.01)

(58) Field of Classification Search
CPC .............. A61K 9/0019; A61K 38/4893; C12Y 304/24069
USPC ...................................... 424/94.67
See application file for complete search history.

(56) References Cited

U.S. PATENT DOCUMENTS

| | | |
|---|---|---|
| 4,921,757 A | 5/1990 | Wheatley et al. |
| 5,437,291 A | 8/1995 | Pasricha et al. |
| 5,670,484 A | 9/1997 | Binder |
| 5,674,205 A | 10/1997 | Pasricha et al. |
| 5,714,468 A | 2/1998 | Binder |
| 5,766,605 A | 6/1998 | Sanders et al. |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,261,572 B1 | 7/2001 | Donovan |
| 6,265,379 B1 | 7/2001 | Donovan |
| 6,299,893 B1 | 10/2001 | Schwartz et al. |
| 6,306,403 B1 | 10/2001 | Donovan |
| 6,306,423 B1 | 10/2001 | Donovan et al. |
| 6,312,708 B1 | 11/2001 | Donovan |
| 6,328,977 B1 | 12/2001 | Donovan |
| 6,337,075 B1 | 1/2002 | Donovan |
| 6,358,513 B1 | 3/2002 | Voet et al. |
| 6,358,917 B1 | 3/2002 | Carruthers et al. |
| 6,358,926 B2 | 3/2002 | Donovan |
| 6,365,164 B1 | 4/2002 | Schmidt |
| 6,383,509 B1 | 5/2002 | Donovan et al. |
| 6,395,277 B1 | 5/2002 | Graham |
| 6,416,765 B1 | 7/2002 | Donovan |
| 6,423,319 B1 | 7/2002 | Brooks et al. |
| 6,458,365 B1 | 10/2002 | Aoki et al. |
| 6,464,986 B1 | 10/2002 | Aoki et al. |
| 6,506,399 B2 | 1/2003 | Donovan |
| 6,585,993 B2 | 7/2003 | Donovan et al. |
| 6,623,742 B2 | 9/2003 | Voet |
| 6,632,440 B1 | 10/2003 | Quinn et al. |
| 6,767,544 B2 | 7/2004 | Brooks |
| 6,787,517 B1 | 9/2004 | Gil et al. |
| 6,838,434 B2 | 1/2005 | Voet |
| 6,869,610 B2 | 3/2005 | Aoki et al. |
| 6,977,080 B1 | 12/2005 | Donovan |
| 7,022,329 B2 | 4/2006 | Donovan |
| 7,048,927 B2 | 5/2006 | Brooks et al. |
| 7,091,176 B2 | 8/2006 | Aoki et al. |
| 7,223,399 B2 | 5/2007 | Brooks et al. |
| 7,361,358 B2 | 4/2008 | Aoki et al. |
| 7,485,624 B2 | 2/2009 | Donovan |
| 7,494,654 B2 | 2/2009 | Brooks et al. |
| 8,105,611 B2 | 1/2012 | Tong et al. |
| 8,470,337 B2 | 6/2013 | Manack et al. |
| 2002/0102274 A1 | 8/2002 | Voet et al. |
| 2003/0165541 A1 | 9/2003 | Donovan |
| 2004/0009180 A1 | 1/2004 | Donovan |
| 2004/0037865 A1 | 2/2004 | Miller |
| 2004/0086531 A1 | 5/2004 | Barron |
| 2005/0147626 A1 | 7/2005 | Blumenfeld |
| 2005/0152905 A1 | 7/2005 | Omoigui |
| 2005/0191321 A1 | 9/2005 | Turkel et al. |
| 2005/0266029 A1 | 12/2005 | Aoki et al. |
| 2006/0083758 A1 | 4/2006 | Dadas |
| 2006/0121057 A1 | 6/2006 | Turkel et al. |
| 2006/0216313 A1 | 9/2006 | Brooks et al. |
| 2006/0286127 A1 | 12/2006 | Van Schaack |
| 2007/0048334 A1 | 3/2007 | Aurora |

(Continued)

FOREIGN PATENT DOCUMENTS

| | | |
|---|---|---|
| EP | 0605501 | 4/1999 |
| WO | 1995-017904 | 7/1995 |

(Continued)

OTHER PUBLICATIONS

Mahowald et al. Long term effects of intra-articular botulinum toxin A for refractory joint pain. Neurotoxicity Research. 2006;9(2,3):179-188.*
Boon et al. Efficacy of intra-articular botulinum toxin type A in painful knee osteoarthritis: a pilot study. PM R. 2010;2:268-276.*
Albanese, A. et al, The Use of Botulinum Toxin on Smooth Muscles, Eur. J. Neurol., Nov. 1995, 29-33, 2 (Supp 3).
Aoki, Roger Kei et al, Mechanisms of the Antinociceptive Effect of Subcutaneous Botox Inhibition of Peripheral and Central Nociceptive Processing, Cephalalgia, 2003, 649 (1 Page), 23.
Arthritis Special Report: Botox and Knee Osteoarthritis, 2007, 2 Pages.
Asada, Kanji et al, Clinical Application of GaAlAs 830 NM Diode Laser in Treatment of Rheumatoid Arthritis, Laser Therapy, 1991, 77-82, 3.

(Continued)

*Primary Examiner* — Lynn Y Fan
(74) *Attorney, Agent, or Firm* — Brigitte C. Phan

(57) ABSTRACT

Methods for modifying progression of osteoarthritis by local administration of a clostridial derivative, such as a botulinum toxin, to an arthritis-affected site are disclosed herein.

10 Claims, 4 Drawing Sheets

(56) References Cited

U.S. PATENT DOCUMENTS

| | | | |
|---|---|---|---|
| 2007/0160633 A1* | 7/2007 | First | A61K 31/167 424/239.1 |
| 2008/0057084 A1 | 3/2008 | Burstein et al. | |
| 2009/0232850 A1* | 9/2009 | Manack et al. | 424/239.1 |

FOREIGN PATENT DOCUMENTS

| | | |
|---|---|---|
| WO | 1995-028171 | 10/1995 |
| WO | WO20020040506 A2 | 5/2002 |
| WO | 2004-041303 | 5/2004 |
| WO | 2004-050621 | 6/2004 |
| WO | 2005-051291 | 6/2005 |

OTHER PUBLICATIONS

Balkwill, F. et al, Cytokine Amplification and Inhibition of Immune and Inflammatory Responses, Journal of Viral Hepatitis, 1997, 6-15, 4(Suppl. 2).

Bigalke, H. et al, Botulinum A Neurotoxin Inhibits Non-Cholinergic Synaptic Transmission in Mouse Spinal Cord Neurons in Culture, Brian Research, 1985, 318-324, 360.

Bigalke, H. et al, Tetanus Toxin and Botulinum A Toxin Inhibit Release and Uptake of Various Transmitter, as Studied with Particulate Preparations From Rat Brain and Spinal Cord, Naunyn Schmiedebergs Arch Pharmacol, 1981, 244-251, 316.

Binz, Thomas et al, The Complete Sequence of Botulinum Neurotoxin Type A and Comparison with Other Clostridial Neurotoxins, Gene Therapy and Molecular Biology, 1990, 9153-9158, 265(16).

Borodic, Gary et al, Clinical and Scientific Aspects of Botulinum A Toxin, Ophthalm Clincs of N America, Sep. 1991, 491-503, 4(3).

Boyd, R.S. et al, The Effect of Botulinum Neurotoxin-B on Insulin Release From a ß-Cell Line, Mov. Disord., May 1995, 376 (abstract), 10 (3).

Boyd, R.S. et al, The Insulin Secreting ß-cell Line, HIT-15, Contains SNAP-25 Which is a Target for Botulinum Neurotoxin-A, Mov. Disord., May 1995, 376, 10(3).

Brin, Mitchell, Interventional Neurology: Treatment of Neurological Conditions with Local Injection of Botulinum Toxin, Arch. de Neurobial, 1991, 7-23, 54.

Bushara, Khalafalla, Botulinum Toxin and Rhinorrhea, Head and Neck Surgery, 1996, 507, 114(3).

Chevalier, X. et al, Intraarticular Injection of Anakinra in Osteoarthritis of the Knee: A Multicenter, Randomized, Double-Blind, Placebo-Controlled Study, Arthritis & Rheumatism, Mar. 2009, 344-352, 61(3).

Chevalier, Xavier, Intraarticular Treatments for Osteoarthritis: New Perspectives, Current Drug Targets, 2010, 546-560, 11.

Choy, Ernest et al, Cytokine Pathways and Joint Inflammation in Rheumatoid Arthritis, N. Engl. J. Med., Mar. 22, 2001, 907-916, 344(12).

Coffield, Julie et al, The Site and Mechanism of Action of Botulinum Neurotoxin, Neurological Disease and Therapy, 1994, 2-10, 25.

Colombo, Mario et al, Cytokine Gene Transfer in Tumor Inhibition and Tumor Therapy: Where Are We Now, Immunol Today, Feb. 1994, 48-51, 15(2).

Dabrowski, E. et al, Botulinum Toxin as a Novel Treatment for Self Mutilation in Lesch-Nyhan Syndrome, Ann Neurol, Sep. 2002, 1 page, 52 (3).

Dykstra, Dennis et al, Treatment of Detrusor-Sphincter Dyssynergia With Botulinum A Toxin: A Double-Blind Study, Arch Phys Med Rehabil, Jan. 1990, 24-26, 71.

Eaker, Ervin et al, Untoward Effects of Esophageal Botulinum Toxin Injection in the Treatment of Achalasia, Digestive Diseases and Sciences, Apr. 1997, 724-727, 42(4).

Fox, David, Cytokine Blockade as a New Strategy to Treat Rheumatoid Arthritis, Arch Intern Med, 2000, 437-444, 160.

Friedenberg, Frank et al, The Use of Botulinum Toxin for the Treatment of Gastrointestinal Motility Disorders, Digestive Diseases and Sciences, 2004, 165-175, 49 (2).

Gonelle-Gispert, Carmen et al, SNAP-25a and -25b Isoforms are Both Expressed in Insulin-Secreting Cells and Can Function in Insulin Secretion, Biochem. J., 1999, 159-165, 339.

Gray, Elaine et al, Inhibition of Tissue Factor and Cytokine Release, Haemostasis, 1996, 92-95, 26(1).

Gui, D. et al, Effects of Botulinum Toxin on Gastric Emptying and Digestive Secretions. A Possible Tool for Correction of Obesity?, Arch Pharmacol, Jun. 2002, 55, 365(2).

Gui, D. et al., Botulinum Toxin Injected in the Gastric Wall Reduces Body Weight and Food Intake in Rats, Alimentary Pharmacology & Therapeutics, Jun. 2000, 829-834, 14, US.

Habermann, E. et al, 125I-Labeled Neurotoxin from Clostridium Botulinum A:Preparation, Bindingto Synaptosomes and Ascent to the Spinal Cord, 1974, 47-56, 281.

Habermann, E. et al, Inhibition by Tetanus and Botulinum A Toxin of the Release of [3H]noradrenaline and [3H] GABA From Rat Brian Homogenate, Experientia, Mar. 1988, 224-226, 44(3).

Habermann, Ernst, Tetanus Toxin and Botulinum A and C Neurotoxins Inhibit Noradrenaline Release from Cultured Mouse Brain, 1988.

Hambleton, Peter, Clostridium botulinum toxins: a general review of involvement in disease, structure,mode of action and preparation for clinical use, Journal of Neurology, 1992, 16-20, 239.

Harrison's Principles of Internal Medicine (1998), Edited by Anthony Fauci et al., 14th Edition, Published by McGraw Hill.

Higgs, G.A., Novel Approaches to the Inhibition of Cytokine Responses in Asthma, J. Pharm Pharmacol., 1997, 25-31, 49(3).

Huang, Xiaohang et al, Truncated SNAP-25 (1-197), Like Botulinum Neurotoxin A, Can Inhibit Insulin Secretion From HIT-T15 Insulinoma Cells, Molecular Endocrinology, 1998, 1060-1070, 12.

Ishikawa, Hitoshi et al, Presynaptic Effects of Botulinum Toxin Type A on the Neuronally Evoked Responses of Albino and Pigmented Rabbit Iris Sphincter and Dilator Muscles, Japan Journal of Ophthalmology, 2000, 106-109, 44.

Jacks, Laura et al, Idiopathic Toe Walking: Treatment with Botulinum Toxin A Injection, Dev Med Child Neurol, 2002, 6, 44 (91).

Jankovic, J., Pharmacology and Histology of the TherapeuticApplication of Botulinum Toxin, 1994, 119-157, 25.

Katsambas, Andreas et al, Cutaneous Diseases of the Foot: Unapproved Treatments, Clin Dermtol, 2002, 689-699, 20(6).

Keir, James, Botulinum Toxin-Physiology and Applications in Head and Neck Disorders, Neck & Head, Jun. 2005, 525-535.

Khawaja, Hassan et al, Botox in Dermatology, International Journal of Dermatology, 2001, 311-317, 40.

Kohl, A. et al, Comparison of the Effect of Botulinum Toxin A (Botox (R)) With the Highly-Purified Neurotoxin (NT 201) in the Extensor Digitorum Brevis Muscle Test, Mov Disord, 2000, 165 Abstract P805, 15(3).

Kondo, T. et al, Modification of the Action of Pentagastrin on Acid Secretion by Botulinum Toxin, Experientia, 1977, 750-751, 33.

Kumar, R. et al, Long-term Safety, Efficacy, and Dosing of Botulinum Toxin Type B (Myobloc) in Cervical Dystonia (CD) and Other Movement Disorders, Mov Disord, 2002, S292-S293, 17 (5).

Lacy, Brian et al, The Treatment of Diabetic Gastroparesis With Botulinum Toxin Injection of the Pylorus, Diabetes Care, Oct. 2004, 2341-2347, 27(10).

Mahowald, Maren et al, Long Term Effects of Intra-Articular Botulinum Toxin A for Refractory Joint Pain, Neurotoxicity Research, 2006, 179-188, 9(2).

Mann, Denise, Botox May Cut Knee Osteoarthritis Pain, 2006, 9 Pages.

Marjama-Lyons, Jill et al, Tremor-Predominant Parkinson's Disease: Approaches to Treatment, Drugs & Aging, Apr. 2000, 273-278, 16(4).

Matsushima, K., Involvement of Leukotactic Activated Cytokine Farmily, Chemokines, in Human Diseases and Their Inhibition, Nihon Rinsho Meneki Gakkai Kaishi, 1996, 552-554, 19(6).

Meyer K.E., A Comparative Systemic Toxicity Study of Neurobloc in Adult and Juvenile Cynomolgus Monkeys, Mov Disord, 2000, 54, 15 (2).

(56) References Cited

OTHER PUBLICATIONS

Miller, Larry et al, Treatment of Idiopathic Gastroparesis With Injection of Botulinum Toxin Into the Pyloric Sphincter Muscle, American Journal of Gastroenterology, 2002, 1653-1660, 97(7).

Moulian, N. et al, Respective Role of Thymus and Muscle in Autoimmune Myasthenia Gravis, Annals New York Academy of Sciences, 1998, 397-406.

Moyer, Elizabath et al, Botulinum Toxin Type B: Experimental and Clinical Experience, Neurological Disease and Therapy, 1994, 71-85, 25.

Naumann, Markus et al, Botulinum Toxin Type A in the Treatment of Focal, Axillary and Palmar hyperhidrosis and Other Hyperhidrotic Conditions, European Journal of Neurology, 1999, S111-S115, 6 (4).

Nishimoto, N. et al, New Therapeutic Strategy for Autoimmune Diseases. 3) Treatment of Autoimmune Diseases by Cytokine Signal Transduction Inhibition, Nippon Naika Gakkai Zasshi, Sep. 1998, 1745-1750, 87(9).

Pearce, Bruce et al, Pharmacologic Characterization of Botulinum Toxin for Basic Science and Medicine, Toxicon, 1997, 1373-1412, 35(9).

Pelletier, Jean-Pierre et al, Strontium Ranelate Reduces the Progression of Experimental Dog Osteoarthritis by Inhibiting the Expression of Key Proteases in Cartilage and of IL-1ß in the Synovium, Ann Rheum Dis, Sep. 2012, 250-257, 72.

Qureshi, Waqar, Gastrointestinal Uses of Botulinum Toxin, J Clin Gastroenterol, 2002, 126-128, 34(2).

Ragona, Rosario Marchese et al, Management of Parotid Sialocele With Botulinum Toxin, Laryngoscope, 1999, 1344-1346, 109(8).

Reginster, Jean-Yves et al, Efficacy and Safety of Strontium Ranelate in the Treatment of Knee Osteoarthritis: Results of a Double-Blind, Randomised Placebo-Controlled Trial, Ann Rheum Dis, 2013, 179-186, 72.

Rogers, John et al, Injections of Botulinum Toxin A in Foot Dystonia, Neurology, Apr. 1993, A329, 43(4).

Rohrbach, Saskia et al, Botulinum Toxin Type A Induces Apoptosis in Nasal Glands of Guinea Pigs, Ann Otol Rhinol Laryngol, 2001, 1045-1050, 110(11).

Rohrbach, Saskia et al, Minimally Invasive Application of Botulinum Toxin Type A in Nasal Hypersecretion, J Oto-Rhino-Laryngol, 2001, 282-284, 63(6).

Rossi, S. et al, Immunohistochemical Localization of SNAP-25 Protein in the Stomach of Rat, Arch Pharmacol, 2002, 113 (Abstract), 365(2).

Sanchez-Prieto, Jose et al, Botulinum Toxin A Blocks Glutamate Exocytosis From Guinea-Pig Cerebral Cortical Synaptosomes, Eur J Biochem, Jun. 1987, 675-681, 165(3).

Schantz, Edward et al, Preparation and Characterization of Botulinum Toxin Type A for Human Treatment, Neurological Disease and Therarpy, 1994, 41-49, 25, US.

Schantz, Edward J. et al, Properties and Use of Botulinum Toxin and Other Microbial Nerotoxins in Medicine, Microbiological Reviews, Mar. 1992, 80-99, 56 (1).

Schwiebert, Lisa et al, Glucocorticosteroid Inhibition of Cytokine Production: Relevance to Antiallergic Actions, J. Allergy Clin Immunol, Jan. 1996, 143-152, 97(1).

Sevim, Serhan et al, Botulinum Toxin—A Therapy for Palmar and Plantar Hyperhidrosis, Acta Neurol Belg, Dec. 2002, 167-170, 102(4).

Simpson, Lance, The Origin, Structure, and Pharmacological Activity of Botulinum Toxin, Pharmcol Rev, 1981, 155-188, 33(3).

Singh, Bal Ram, Critical Aspects of Bacterial Protein Toxins, Natural Toxins II, 1996, 63-84, Chapter 4.

Sloop, Richard et al, Reconstituted Botulinum Toxin Type A Does Not Lose Potency in Humans if it is Refrozen or Refrigerated for 2 Weeks Before Use, Neurology, 1997, 249-253, 48.

Stassmann, Gideon et al, Inhibition of Experimental Cancer Cachexia by Anti-Cytokine and Anti-Cytokine-Receptor Therapy, Cytokines and Molecular Therapy, 1995, 107-113, 1.

Suputtitada, A., Local Botulinum Toxin Type A Injections in the Treatment of Spastic Toes, Am J Phys Med Rehabil, Oct. 2002, 770-775, 81(10).

Ueno, S. et al, Acetylcholine Receptor in Rabbit Thymus: Antigenic Similarity Between Acetylcholine Receptors of Muscle and Thymus, Clin. Exp. Immunol., 1980, 463-469, 42.

Verheyden, Jean et al, Other Noncosmetic Uses of BOTOX, Dis Mon, 2002, 357-366, 48.

Wang, Zhishun et al, Effects of Botulinum Toxin on Gastric Myoelectrical and Vagal Activities in Dogs, Gastroenterology, Apr. 2001, 3869, 120 (5).

Weyand, Cornelia et al, T-cell responses in rheumatoid arthritis: systemic abnormalities-local disease, Curr Op Rheumatol, 1999, 210-217, 11.

Widmer, Michael B., Inhibition of cytokine function: potential in autoimmune disease, Current Opinion in Biotechnology, 1991, 872-876, 2.

Wiegand, H. et al, 125 I-Labelled Botulinum. A Neurotoxin: Pharmacokinetics in Cats after Intramuscular Injection, Arch Pharmacol, 1976, 161-165, 292.

Wiesel, P.H. et al, Botulinum Toxin for Refractory Postoperative Pyloric Spasm, Endoscopy, 1997, 132, 29(2).

Zhao, Xiaotuan et al, Botulinum Toxin for Spastic GI Disorders: A Systematic Review, Gastrointestinal Endoscopy, 2003, 219-235, 57 (2).

David J. Hunter, Pharmacologic therapy for osteoarthritis—the era of disease modificaiton, Nature Reviews/Rheumatology Jan. 2011, p. 13-22, vol. 7, Macmillian Publishers Limited.

Chou, C.C. et al, Analgesic and Biomechanical Effects of Intra-Articular Botulinum Toxin Type a in Chronic Knee Osteoarthritis, Database Compendex, Engineering Information, 2010, 1 Page.

Hadley, H.S. et al, Effects of Intra-Articular Botulinum Toxin Type A (BOTOX) in Dogs With Chronic Osteoarthritis, Database Medline, US National Library of Medicine, 2010, 1 Page, 23(4).

Namazi, Hamid et al, Botulinum Toxin and Osteoarthritis: Greater Expectations, Medical Hypotheses, 2007, 1188, 68(5).

Namazi, Hamid et al, Botulinum Toxin as a Novel Addition to Anti-Arthritis Armamentarium: An Experimental Study in Rabbits, International Immunopharmacology, 2006, 1743-1747, 6.

Brockmann, K. et al., "Comparison of different preparations of botulinumtoxin A in the treatment of cervical dystonia", Neurology Asia, vol. 17, No. 2, pp. 115-119 (Jun. 2012).†

Talarico-Filho, et al., A double-blind randomized, comparative study of two type A botulinum toxins in the treatment of primary axillary hyperhidrosis of primary acillary hyperhidrosis Dermatologic Surgery, vol. 33, Supplement #1, pp. S44-S.†

Marion, M-H., et al., "Dose standardisation of botulinum toxin", Journal of Neurology, Neurosurgery & Psychiatry, vol. 59, No. 1, pp. 102-103 (Jul. 1995).†

Chou, C-L et al., "Therapeutic effects of intra-articular botulinum neurotoxin in advance knee osteoarthritis", Journal of the Chinese Medical Association, vol. 73, No. 11, pp. 573-580 (Nov. 2010).†

Boon, A.J. et al., "Efficacy of intra-articular botulinum toxin type A in painful knee osteoarthritis: a pilot study", Physical Medicine & Rehabilitation, vol. 2, Issue 4, pp. 268-276 (Apr. 2010).†

\* cited by examiner
† cited by third party

METHODS FOR MODIFYING PROGRESSION OF OSTEOARTHRITIS

FIELD

The present disclosure relates to methods for treatment of arthritis. In particular, the present disclosure relates to methods of modifying progression of arthritis using clostridial derivatives.

BACKGROUND

Arthritis is one of the most prevalent chronic health problems and one of the most common causes of disability in America. It affects over 45 million adults in the United States. This number is anticipated to rise to 60 million, or 18% of the population, by 2020. There are more than 127 different types of arthritis as defined by the Arthritis Foundation, including osteoarthritis, rheumatoid arthritis, psoriatic arthritis, septic arthritis and related autoimmune diseases. Regardless of the type of arthritis, common symptoms for all arthritis disorders include varied levels of pain, swelling, functional limitation and joint stiffness. Arthritic disorders such as lupus and rheumatoid can also affect other organs in the body.

To date, no targeted treatments for alleviating, protecting or improving cartilage or other structural damage of arthritis are available. The goals of current therapies for arthritis, including osteoarthritis, are to alleviate pain and other related arthritis associated symptoms. Current therapies for managing osteoarthritis pain include oral analgesics or corticosteroids, localized treatments with topical analgesics (e.g., NSAIDs, capsaicin), intra-articular injections of corticosteroids or viscosupplements. Oral analgesics have substantial limitations because they may not provide sufficient pain relief and often produce intolerable side effects, for example, gastrointestinal bleeding and renal toxicity for regular NSAIDS users, addiction or breathing suppression for opioids; and adverse drug interactions. Localized corticosteroid injections may reduce pain for a short period (1-3 weeks), but have long term side effects, including cartilage break down, Cushing's syndrome; furthermore they are intolerable to patients with diabetic mellitus. Viscosupplement administration, such as hyaluronic acid, while well-tolerated, is not always effective.

While the current therapies may provide short term relief for pain and other osteoarthritis associated symptoms, they do not address the underlying structural problem. None of the available treatments can halt or slow down progression of arthritis, such as osteoarthritis, once cartilage and/or other structural damage occurs. Thus, there is a need for treatment methods that modify progression of arthritis, such as osteoarthritis.

SUMMARY

Aspects of the present disclosure provide methods for modifying progression of arthritis, such as osteoarthritis. In some aspects, the present disclosure provides a method for treating osteoarthritis by mitigating or reversing osteoarthritis associated structural damages. In some aspects, the present disclosure provides a method for slowing down progression of osteoarthritis. In some aspects, the present disclosure provides a method for modifying progression of osteoarthritis by reducing the levels and/or activities of one or more cartilage-degrading agents, increasing the levels of one or more cartilage-forming components, or both.

In one aspect, the present disclosure provides a method for treating osteoarthritis in a patient in need thereof, the method comprises locally administering a therapeutically effective amount of a clostridial derivative to an osteoarthritis-affected site of the patient, thereby treating osteoarthritis in the patient; wherein the administering reduces the levels of at least one cartilage-degrading agent, increasing the levels of at least one cartilage-forming component, or both.

In another aspect, the present disclosure provides a method for delaying progression of osteoarthritis or repairing cartilage defect in a patient in need thereof, the method comprises modifying the levels of at least one cartilage-forming component, one cartilage-degrading agent, or both, by locally administering a therapeutically effective amount of a clostridial derivative to an osteoarthritis-affected site of the patient, thereby delaying progression of osteoarthritis or repairing cartilage defect in the patient.

In yet another aspect, the present disclosure provides a method for reversing cartilage breakdown in a patient suffering from osteoarthritis, the method comprises modifying the levels and/or activities of at least one agent associated with osteoarthritis-mediated cartilage breakdown, by locally administering a therapeutically effective amount of a clostridial derivative to an osteoarthritis-affected site of the patient, thereby reversing cartilage breakdown in the patient. In some embodiments, the at least one agent associated with osteoarthritis-medicated cartilage breakdown comprises a cartilage-degrading agent, a cartilage-forming component, or mixtures thereof.

In yet another aspect, the present disclosure provides a method for modifying the levels and/or activities of at least one agent associated with osteoarthritis-mediated cartilage degradation, the method comprises locally administering a therapeutically effective amount of a botulinum toxin type A to an osteoarthritis-affected site of the patient, thereby mitigating the osteoarthritis-mediated cartilage degradation. In some embodiments, the present method reduces the levels and/or activities of at least one cartilage-degrading agent. In some embodiments, the present method increases the levels and/or activities of at least one cartilage-forming component. In some embodiments, the present method reduces the levels and/or activities of at least one cartilage-degrading agent and increases the levels and/or activities of at least one cartilage-forming component.

BRIEF DESCRIPTION OF THE FIGURES

The following drawings are presented to illustrate aspects and features of embodiments of the present invention.

DETAILED DESCRIPTION

Figure 1:
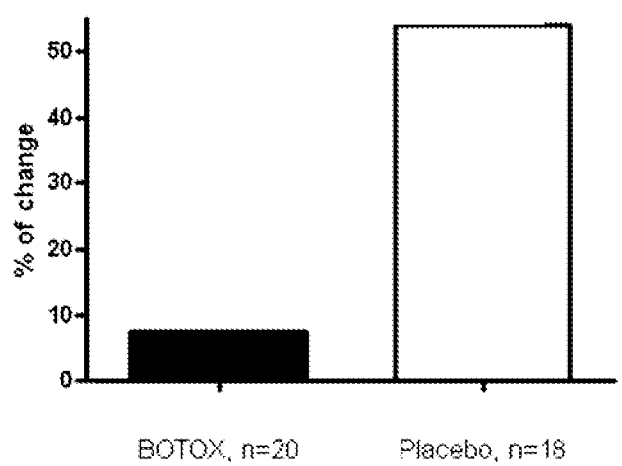
FIG. 1 shows the relative change from baseline over 12-week period in matrix metalloproteinase-1 (MMP-1) levels after treatment with an exemplary clostridial derivative or with a placebo in patients with primary knee osteoarthritis.

In some aspects, the present disclosure provides a method for delaying progression of arthritis, including osteoarthritis (OA), rheumatoid arthritis (RA), psoriatic arthritis and the like in a patient.

Arthritis

Arthritis is a form of joint disorder that involves inflammation of one or more joints. Normal articular cartilage consists of an extensive hydrated extracellular matrix. The matrix consists mainly of collagen and proteoglycans, principally aggrecan, which is large and aggregates with hyaluronic acid. Embedded in the extracellular matrix are the chondrocytes, which regulate the synthesis and degradation of the articular cartilage. In normal articular cartilage, the extracellular matrix is constantly being degraded and synthesized. Collagen and cartilage proteoglycans are degraded by various proteinases, including metalloproteinases, and collagenases. Under normal circumstances, the activation of these degradative enzymes is held in check by inhibitors, such as tissue inhibitor of metalloproteinases (TIMPs) and plasminogen activator inhibitor-7 (PAI-7). The balance of metalloproteinases (MMPs) and inhibitors of metalloproteinases (TIMPs) is important to maintain the normal turnover of the extracellular matrix. Under pathological conditions such as for example in Osteoarthritis and Rheumatoid arthritis, mechanical and shear stress, inflammatory cytokines (e.g., IL-1, IL-6 and tumor necrosis factor-α) and/or growth factors disrupt this balance and promote the synthesis of MMPs and inhibit the expression of TIMPs. Thus, collagen and aggrecan degradation will outweigh the synthesis and deposition by chondrocytes, which ultimately results in cartilage defect. Inflammation can occur secondary to structural damage as in osteoarthritis or is the main cause to incur arthritis with subsequent structural damage as in rheumatoid arthritis.

Osteoarthritis (OA)

Osteoarthritis (OA) is the most common form of arthritis and a leading cause of chronic disability. It can affect both the larger and the smaller joints of the body, including the hands, feet, back, hip, knee and spine. OA is a multifactorial disease, characterized by joint pain, tenderness, limitation of movement, crepitus, occasional effusion, wear or tear of cartilage, wear or tear of meniscus, wear or tear of ligament, subchondral bone lesion, capsule damage and/or hyperplasia of the synovial membrane. Progression of OA is marked by destruction of the joint cartilage, sclerosis or cyst formation of underlying bone, joint space narrowing and formation of osteophytes at the joint margin.

Rheumatoid Arthritis (RA)

Rheumatoid arthritis (RA) is an autoimmune disease that results in a chronic, systemic inflammatory disorder that may affect many tissues and organs, but principally attacks flexible (synovial) joints. It can be a disabling and painful condition, which can lead to substantial loss of functioning and mobility if not adequately treated. Joint cartilage loss and other structural damage is subsequent to inflammatory response at the involved joints. Once cartilage lesion occurs, RA will have a similar disease progression as OA even after the primary inflammation cause is under control.

Botulinum Toxin

Botulinum neurotoxins (BoNTs) such as, for example, BoNT/A, BoNT/B, etc., act on the nervous system by blocking the release of neurosecretory substances such as neurotransmitters at the nerve endings. The action of BoNT is initiated by its binding to a receptor molecule on the cell surface, then the toxin-receptor complex undergoes endocytosis. Once inside the cell, BoNT cleaves exocytotic specific proteins responsible for neurotransmitter docking and release from the cell known as the SNARE proteins (soluble N-ethylmaleimide-sensitive factor attachment protein receptor). The resulting transient chemodenervation has been utilized medically to block motor neurotransmission at the neuromuscular junction leading to a variety of therapeutic applications.

Of the existing serotypes, Botulinum toxin type A is one of the most lethal natural biological agents known to man. About 50 picograms of a commercially available botulinum toxin type A (purified neurotoxin complex, available from Allergan, Inc., of Irvine, Calif. under the trade name BOTOX® in 100 unit vials) is a $LD_{50}$ in mice (i.e. 1 unit). One unit of BOTOX® contains about 50 picograms (about 56 attomoles) of botulinum toxin type A complex. One unit (U) of botulinum toxin is defined as the $LD_{50}$ upon intraperitoneal injection into female Swiss Webster mice weighing 18 to 20 grams each.

Botulinum toxin has become widely investigated for its therapeutic potential in the treatment of a variety of neuromuscular disorders including: blepharospasm, spasmodic dysphonia, Strabismus, hemifacial spasm, and adult onset spasmodic torticollis. (Simpson, 1981; Habermann, 1989; Jankovic and Brin, 1991; Borodic et al., 1991; Hambleton, 1992; Schantz and Johnson, 1992; Valtorta and Arslan 1993). Intramuscular injection of nanogram quantities of purified botulinum toxin results in the toxin binding to presynaptic cholinergic nerve terminals and inhibits the release of acetylcholine and thus decreases muscle activity. The result is relaxation of the tonically contracted muscle and thus relaxation of the intended muscle or muscle group.

Botulinum toxin has been described in a method for treating osteoarthritis associated pain (see e.g. U.S. Pat. No. 8,470,337); wherein the toxin is administered by intramuscular injections into the splenius capitis and temporalis muscles in order to alleviate the osteoarthritis associated pain.

The present disclosure provides a method for modifying progression of arthritis in a patient by local administration of a clostridial derivative to an arthritis-affected site of the patient. In some embodiments, the present method modifies progression of osteoarthritis. In an alternative embodiment, the present method modifies progression of rheumatoid arthritis. In yet alternative embodiments, the present method modifies progression of other types of arthritis.

In some aspects, the present disclosure provides a method for treating osteoarthritis. In some aspects, the present method mitigates or reverses osteoarthritis-associated structural damages, such as cartilage breakdown, thereby modifying progression of osteoarthritis. In some aspects, the present method mitigates or reverses osteoarthritis-associated structural damages by modifying the levels and/or activities of at least one agent associated with osteoarthritis-mediated cartilage deterioration. In some embodiments, the present method reduces the levels and/or activities of one or more cartilage-degrading agents. In some embodiments, the present method increases the levels and/or activities of one or more cartilage-forming components. In some embodiments, the present method modifies the levels and/or activities of cartilage-degrading agents and induces an increase in the levels of cartilage-forming components.

Without wishing to be bound by any theory, progression of OA is marked by progressive destruction of the joint cartilage, which is caused at least in part by an increase in the levels and/or activities of one or more cartilage-degrading agents, and/or a reduction in the synthesis and/or an increase in the breakdown of one or more cartilage-forming-components. Administration of an exemplary clostridial derivative in accordance with aspects of the present method, among other things, reduces the levels, or lessens a level increase associated with OA progression of one or more cartilage-degrading agents. By reducing the levels and/or activities of one or more cartilage-degrading agents, among other things, the present method slows down cartilage breakdown, prevents cartilage breakdown from worsening, reverses cartilage breakdown, or combinations thereof.

In some other aspects, administration of an exemplary clostridial derivative according to aspects of the present method increases the levels of one or more cartilage-forming components. By increasing the levels and/or activities of one or more cartilage-forming components, among other things, the present method prevents cartilage breakdown from worsening, repairs and reverses cartilage breakdown. In some other aspects, by increasing the levels and/or activities of one or more cartilage-forming components, and thus decreasing the cartilage defect area, the present method mitigates or reverses cartilage breakdown and delays progression of osteoarthritis.

In some embodiments, the cartilage-degrading agent includes proteinases and collagenases. In some embodiments, the cartilage-degrading agent includes aspartate proteinases, serine proteinases, metalloproteinases or combinations thereof. In some embodiments, the metalloproteinases comprise matrix metalloproteinase (MMPs) and aggrecanases, such as ADAMTS (a disintegrin and a metalloproteinase with thrombospondin motifs). In one embodiment, the cartilage-degrading agent is a matrix-metalloproteinase, including but not limited to matrix-metalloproteinase-1 (MMP-1), matrix metalloproteinase-3 (MMP-3), matrix-metalloproteinase-9 (MMP-9), matrix-metalloproteinase-13 (MMP-13 or collagenase-3), and the like, or combinations thereof. In alternative embodiments, the cartilage-degrading agent is an aggrecanase, such as an ADAMTS proteinase.

In some embodiments, administration of the clostridial derivative to a patient according to the present method simultaneously reduces the levels of one or more inflammation mediators, such as interleukin-6 (IL-6) and the like. In other embodiments, administration of the clostridial derivative to a patient reduces the levels and/or activities of one or more cartilage-degrading agents and simultaneously increases the levels of inflammation mediators, such as interleukin-6 (IL-6) and the like. In some embodiments, the present method is effective in mitigating the level changes and/or activities of the cartilage-degrading agents independently of inflammation mediators.

In another aspect, the present disclosure provides a method for enhancing cartilage producing activities in an arthritis-affected site of a patient, thereby delaying progression of arthritis or repairing existing cartilage defect. In some embodiments, the present method increases the levels and/or activities of one or more cartilage-forming components. In some embodiments, the cartilage-forming component includes but is not limited to aggrecan, proteoglycan, collagen, hyaluronan, cartilage oligomeric matrix protein (COMP), fibrillin, fibronectin; or combinations thereof.

In some embodiments, administration of the clostridial derivative to a patient according to aspects of the present method increases the levels and/or activities of one or more cartilage-forming components and simultaneously reduces the levels of one or more inflammation mediators, such as interleukin-6 (IL-6) and the like. In other embodiments, the administration of the clostridial derivative increases the levels and/or activities of one or more cartilage-forming components and simultaneously increases the level of inflammation mediators, such as interleukin-6 (IL-6) and the like. In some embodiments, the present method is effective in increasing the levels and/or activities of the cartilage-forming component independently of inflammation mediators.

Thus, aspects of the present disclosure provide a method for modifying the levels and/or activities of at least one agent associated with osteoarthritis-mediated cartilage deterioration, the method comprises locally administering a therapeutically effective amount of a clostridial derivative to an osteoarthritis-affected site of the patient, thereby mitigating the osteoarthritis-mediated cartilage deterioration.

Definitions

As used herein, the words or terms set forth below have the following definitions:

"About" or "approximately" as used herein means within an acceptable error range for the particular value as determined by one of ordinary skill in the art, which will depend in part on how the value is measured or determined, (i.e., the limitations of the measurement system). For example, "about" can mean within 1 or more than 1 standard deviations, per practice in the art. Where particular values are described in the application and claims, unless otherwise stated, the term "about" means within an acceptable error range for the particular value.

"Administration", or "to administer" means the step of giving (i.e. administering) a botulinum toxin to a subject, or alternatively a subject receiving a pharmaceutical composition. The present method can be performed via administration routes including intramuscular, non-intramuscular, intra-articular, extra-articular, peri-articular, intradermal, subcutaneous administration, topical administration (using liquid, cream, gel or tablet formulation), intrathecal administration, intraperitoneal administration, intravenous infusion, implantation (for example, of a slow-release device such as polymeric implant or miniosmotic pump), or combinations thereof.

"Alleviating" means a reduction in arthritis associated structural deterioration. Thus, alleviating includes some reduction, significant reduction, near total reduction, and total reduction. An alleviating effect may not appear clinically for between 1 to 7 days after administration of a clostridial derivative to a patient or sometime thereafter.

"Botulinum toxin" means a neurotoxin produced by *Clostridium botulinum*, as well as a botulinum toxin (or the light chain or the heavy chain thereof) made recombinantly by a non-Clostridial species. The term "botulinum toxin", as used herein, encompasses the botulinum toxin serotypes A, B, $C_1$, D, E, F and G, and their subtypes and any other types of subtypes thereof, or any re-engineered proteins, analogs, derivatives, homologs, parts, sub-parts, variants, or versions, in each case, of any of the foregoing. "Botulinum toxin", as used herein, also encompasses a "modified botulinum toxin". Further "botulinum toxin" as used herein also encompasses a botulinum toxin complex, (for example, the 300, 600 and 900 kDa complexes), as well as the neurotoxic component of the botulinum toxin (150 kDa) that is unassociated with the complex proteins.

"Cartilage-degrading agent" refers to a molecule which is directly or indirectly associated with cartilage degradation or deterioration.

"Cartilage-forming component" refers to a molecule which contributes, directly or indirectly, to the production of cartilage or the extracellular matrix.

"Clostridial derivative" refers to a molecule which contains any part of a clostridial toxin. As used herein, the term "clostridial derivative" encompasses native or recombinant neurotoxins, recombinant modified toxins, fragments thereof, a Targeted vesicular Exocytosis Modulator (TEM), or combinations thereof.

"Clostridial toxin" refers to any toxin produced by a Clostridial toxin strain that can execute the overall cellular mechanism whereby a Clostridial toxin intoxicates a cell and encompasses the binding of a Clostridial toxin to a low or high affinity Clostridial toxin receptor, the internalization of the toxin/receptor complex, the translocation of the Clostridial toxin light chain into the cytoplasm and the enzymatic modification of a Clostridial toxin substrate.

"Effective amount" as applied to the biologically active ingredient means that amount of the ingredient which is generally sufficient to induce a desired change in the subject.

"Implant" means a controlled release (e.g., pulsatile or continuous) composition or drug delivery system. The implant can be, for example, injected, inserted or implanted into a human body.

"Intra-articular injection" refers to an injection directly into a joint or into a portal.

"Extra-articular injection" refers to an injection outside of a joint space.

"Peri-articular injection" refers to an injection to an area around a joint.

"Local administration" means administration of a clostridial derivative to or to the vicinity of an arthritis-affected site in a patient by a non-systemic route. Thus, local administration excludes systemic routes of administration, such as intravenous or oral administration.

"Peripheral administration" means administration to a location away from a symptomatic location, as opposed to a local administration.

"TEMs", abbreviated for Targeted Exocytosis Modulators are retargeted endopeptidases that direct the catalytic activity of the light chain to specific types of neuronal cells or to target cells that were not affected by botulinum toxins expanding the beneficial clinical effect of inhibition of exocytosis in several human diseases.

"Treating" or "treatment" means to alleviate (or to eliminate) an undesirable condition, for example cartilage deterioration, either temporarily or permanently.

"Therapeutically effective amount" refers to an amount sufficient to achieve a desired therapeutic effect. The therapeutically effective amount usually refers to the amount administered per injection site per patient treatment session, unless indicated otherwise.

Aspects of the present disclosure provide a method for delaying progression of arthritis and/or correcting existing cartilage defects in a patient in need thereof, the method comprises administering a therapeutically effective amount of a clostridial derivative to an arthritis-affected site of the patient. In some embodiments, the present method reduces cartilage breakdown activities or prevents cartilage breakdown from worsening. In some embodiments, the present method modifies the levels and/or activities of one or more agents associated with arthritis-mediated structural deterioration. In some embodiments, the present modifies progression of osteoarthritis. In some embodiments, the present method delays progression of rheumatoid of arthritis. In yet alternative embodiments, the present method delays progression of other types of arthritis.

In some embodiments, the arthritis-affected site or osteoarthritis-affected site includes a knee joint, a hip joint, a hand joint, a shoulder joint, an ankle joint, a foot joint, an elbow joint, a wrist joint, a sacroiliac joint, a spine joint, or combinations thereof.

In some embodiments, the clostridial derivative is administered directly into a joint cavity or structural components surrounding the joint cavity, or both. In some embodiments, the administration of the clostridial derivative is by intra-articular, extra-articular, peri-articular injections, or combinations thereof.

Intra-articular administration sites include the cavity of the affected joint, a medial supra-patellar portal, medial or lateral mid-patellar portals and medial or lateral infra-patellar portals, or combinations thereof. Peri-articular delivery sites include: infra-patellar fat pad, quadriceps fat pad, anterior suprapatellar fat pad, subcutaneous space, subcutaneous bursa, intra-articular bursa, cruciate ligaments if present, menisci if present, medial and/or lateral collateral ligaments, capsule, periosteum in the joint, bone morrow; tendons surrounding the joint; intra-venous infusion. In alternative embodiments, the administration route is by intramuscular, non-intramuscular, intradermal, subcutaneous administration, intrathecal administration, intraperitoneal administration, implantation, or combinations thereof.

Intra-articular administration of the clostridial derivative to the affected site can be guided by fluoroscopy or ultrasonography, as well known to one of ordinary skills in the art. For deeper joints such as the hip, imaging guidance is crucial. To limit the risk of inaccurate needle placement, the present method further comprises aspirating synovial fluid within the joint cavity prior to administration of the clostridial derivative.

In some embodiments, the clostridial derivative of the present method includes a native, recombinant clostridial toxin, recombinant modified toxin, fragments thereof, targeted exocytosis modulators (TEMs), or combinations thereof. In some embodiments, the clostridial derivative is a botulinum toxin. In alternative embodiments, the clostridial derivative is a TEM.

In some embodiments, the botulinum neurotoxin can be a modified neurotoxin, that is a botulinum neurotoxin which has at least one of its amino acids deleted, modified or replaced, as compared to a native toxin, or the modified botulinum neurotoxin can be a recombinant produced botulinum neurotoxin or a derivative or fragment thereof. In certain embodiments, the modified toxin has an altered cell targeting capability for a neuronal or non-neuronal cell of interest. This altered capability is achieved by replacing the naturally-occurring targeting domain of a botulinum toxin with a targeting domain showing a selective binding activity for a non-botulinum toxin receptor present in a non-botulinum toxin target cell. Such modifications to a targeting domain result in a modified toxin that is able to selectively bind to a non-botulinum toxin receptor (target receptor) present on a non-botulinum toxin target cell (re-targeted). A modified botulinum toxin with a targeting activity for a non-botulinum toxin target cell can bind to a receptor present on the non-botulinum toxin target cell, translocate into the cytoplasm, and exert its proteolytic effect on the SNARE complex of the target cell. In essence, a botulinum toxin light chain comprising an enzymatic domain is intracellularly delivered to any desired cell by selecting the appropriate targeting domain.

In some embodiments, the clostridial derivative is a botulinum toxin, which is selected from the group consisting of botulinum toxin types A, B, $C_1$, D, E, F and G. In one embodiment, the clostridial derivative of the present method is a botulinum toxin type A. The botulinum toxin can be a recombinantly made botulinum neurotoxins, such as botulinum toxins produced by E. coli.

The clostridial derivative, such as a botulinum toxin, for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as, for example, albumin, or the like. Acceptable excipients or stabilizers include protein excipients, such as albumin or gelatin, or the like, or non-protein excipients, including poloxamers, saccharides, polyethylene glycol, or the like. In embodiments containing albumin, the albumin can be, for example, human serum albumin or recombinant human albumin, or the like. The lyophilized material can be reconstituted with a suitable liquid such as, for example, saline, water, or the like to create a solution or composition containing the botulinum toxin to be administered to the patient.

In some embodiments, to increase the resident time of the clostridial derivative in the joint, the clostridial derivative is provided in a controlled release system comprising a polymeric matrix encapsulating the clostridial derivative, wherein fractional amount of the clostridial derivative is released from the polymeric matrix over a prolonged period of time in a controlled manner. Controlled release neurotoxin systems have been disclosed for example in U.S. Pat. Nos. 6,585,993; 6,585,993; 6,306,423 and 6,312,708, each of which is hereby incorporated by reference in its entirety.

The therapeutically effective amount of the clostridial derivative, for example a botulinum toxin, administered according to the present method can vary according to the potency of the toxin and particular characteristics of the condition being treated, including its severity and other various patient variables including size, weight, age, and responsiveness to therapy. The potency of the toxin is expressed as a multiple of the LD50 value for the mouse, one unit (U) of toxin being defined as being the equivalent amount of toxin that kills 50% of a group of 18 to 20 female Swiss-Webster mice, weighing about 20 grams each.

The therapeutically effective amount of the botulinum toxin according to the present method can vary according to the potency of a particular botulinum toxin, as commercially available Botulinum toxin formulations do not have equivalent potency units. For example, one unit of BOTOX® (onabotulinumtoxinA), a botulinum toxin type A available from Allergan, Inc., has a potency unit that is approximately equal to 3 to 5 units of DYSPORT® (abobotulinumtoxinA), also a botulinum toxin type A available from Ipsen Pharmaceuticals. In some embodiments, the amount of abobotulinumtoxinA, (such as DYSPORT®), administered in the present method is about three to four times the amount of onabotulinumtoxinA (such as BOTOX®) administered, as comparative studies have suggested that one unit of onabotulinumtoxinA has a potency that is approximately equal to three to four units of abobotulinumtoxinA. MYOBLOC®, a botulinum toxin type B available from Elan, has a much lower potency unit relative to BOTOX®. In some embodiments, the botulinum neurotoxin can be a pure toxin, devoid of complexing proteins, such as XEOMIN® (incobotulinumtoxinA). One unit of incobotulinumtoxinA has potency approximately equivalent to one unit of onabotulinumtoxinA. The quantity of toxin administered and the frequency of its administration will be at the discretion of the physician responsible for the treatment and will be commensurate with questions of safety and the effects produced by a particular toxin formulation.

In some embodiments, the present method comprises administering a therapeutically effective amount of the clostridial derivative per injection site (or osteoarthritis-affected site) per patient treatment session. In some embodiments, the therapeutically effective amount is the amount which prevents an increase in the levels of at least one cartilage-degrading agent. In some other embodiments, the therapeutically amount is the amount which effectively reduces the levels and/or activities of at least one cartilage-degrading agent. In some embodiments, the therapeutically effective amount is the amount sufficient to induce an increase in the levels of at least one cartilage-forming component. In some embodiments, the therapeutically effective amount can be determined by measuring changes in the levels of at least one cartilage-degrading agent and/or changes in the levels of at least one cartilage-forming component in a group of patients prior and after administration of a clostridial derivative relative to a control group, i.e. the group of patients who did not receive the clostridial derivative administration. In some embodiments, the therapeutically effective amount can be determined by measuring changes in the levels of at least one cartilage-degrading agent in a patient prior and after administration of a clostridial derivative. In some other embodiments, the therapeutically effective amount can be determined by measuring the pain score of a patient prior and after administration of a clostridial derivative. In some embodiments, the therapeutically effective amount is determined by a combination of one or more of the above.

In some embodiments, the therapeutically effective amount ranges from about 2 units to about 800 units of a botulinum toxin type A, such as onabotulinumtoxinA (such as BOTOX®) per injection site per patient treatment session. In some embodiments, the therapeutically effective amount ranges from 10 units to about 100 units of onabotulinumtoxinA. In some embodiments, the therapeutically effective amount ranges from about 150 to about 500 units of onabotulinumtoxinA. In one embodiment, the therapeutically effective amount is about 200 units of onabotulinumtoxinA. In some embodiments, the therapeutically amount ranges from about 500 units to about 800 units of onabotulinumtoxinA.

In some embodiments, the therapeutically effective amount of abobotulinumtoxinA, (such as DYSPORT®), administered according to aspects of the present method is about three to four times the amount of onabotulinumtoxinA (such as BOTOX®). In some embodiments, the therapeutically effective amount of incobotulinumtoxinA, (such as XEOMIN®), administered according to aspects of the present method is similar to the amount of onabotulinumtoxinA (such as BOTOX®) administered, as comparative studies have suggested that one unit of incobotulinumtoxinA has a potency approximately equivalent to one unit of onabotulinumtoxinA.

In some embodiments, the therapeutically effective amount is from about 0.1 to 1000 micrograms (μg) of a TEM (Targeted Exocytosis Modulators).

In some embodiments, the present method comprises administering from about 2 to about 800 units of a botulinum toxin type A, such as BOTOX®, intra-articularly into a joint space, such as for example a knee joint. In some embodiments, the present method comprises administering 50-250 units of onabotulinumtoxinA, such as BOTOX®, intra-articularly into a joint space. In one specific embodiment, the present method comprises administering about 200 units of a botulinum toxin type A intra-articularly into a joint space. In some embodiments, the present method comprises administering about 10-500 units of a botulinum toxin type A into a fat pad, such as the infra-patellar fat pad, the supra-patellar fat pad, or combinations thereof. In one specific embodiment, the present method comprises administering about 10-500 units of a botulinum toxin type A intra-articularly into a joint space and about 10-500 units into a fat pad, such as the infra-patellar fat pad, the supra-patellar fat pad, or combinations thereof. In alternative embodiments, the present method comprises administering about 40-1200 units of DYSPORT® intra-articularly into a joint space and about 40-2000 units of DYSPORT® into a fat pad, such as the infra-patellar fat pad, the supra-patellar fat pad, or combinations thereof. In some embodiments, the present method comprises administering a botulinum toxin type A, and concurrently or sequentially administering a botulinum toxin type B, $C_1$, D, E, F, G, or combinations thereof. In alternative embodiments, the present method comprises administering a botulinum toxin type B, $C_1$, D, E, F, G, or combinations thereof.

In some embodiments, administration of a clostridial derivative according to aspects of the present methods reduces the levels of at least one cartilage-degrading agent from about 10% to about 90%. In some embodiments, the present method reduces the levels of the at least one cartilage-degrading agent by over 90%. In some embodiments, the present method reduces the levels of the at least one-cartilage degrading agent by less than about 10%.

In some embodiments, administration of a clostridial derivative according to aspects of the present methods increases the levels of at least one cartilage-forming component from about 10% to about 90%. In some embodiments, the present method increases the levels of the at least one cartilage-forming component by over 90%. In some embodiments, the present method increases the levels of the at least one-cartilage forming component by less than about 10%.

In some embodiments, the present method comprises administering about 0.1 to 1000 micrograms (μg) of a TEM (Targeted Exocytosis Modulators) intra-articularly into a joint space, such as for example a knee joint. In some embodiments, the present method comprises administering about 20-250 μg of TEM intra-articularly into a joint space. In one specific embodiment, the present method comprises administering about 3-70 μg of TEM intra-articularly into a joint space. In some embodiments, the present method comprises administering about 0.1 to 1000 μg of a TEM into a fat pad, such as the infra-patellar fat pad, the supra-patellar fat pad, or combinations thereof. In one specific embodiment, the present method comprises administering about 0.1 to 1000 μg of a TEM intra-articularly into a joint space and about 0.1 to 1000 μg into a fat pad, such as the infra-patellar fat pad, the supra-patellar fat pad, or combinations thereof.

The effects of the present method can persist for between about 1 month and 5 years. Administration can be modified according to OA progression. In some embodiments, administration of a clostridial derivative according to aspects of the present method is carried out from about 3 months to about 6 months. In some embodiments, increased efficacy of the treatment accorded to the present method is expected to happen when the clostridial derivative is administered according to the disclosed method at about 3 month intervals. In alternative embodiments, the present method can be repeated every 6 months, or 12 months, or 18 months according to progression of osteoarthritis.

In some aspects, the present disclosure provides a method for modifying progression of OA in a patient in need thereof, the method comprises: a) determining baseline levels of at least one agent associated with osteoarthritis-mediated cartilage deterioration (such as a cartilage-degrading agent or a cartilage-forming component), or a baseline pain score, or combinations thereof; b) administering a first therapeutically effective amount of a clostridial derivative to an osteoarthritis-affected site of the patient; c) determining the levels of at least one cartilage-degrading agent, the levels of at least one cartilage-forming agent, or a pain score, or combinations thereof; c) administering a second therapeutically effective amount of the clostridial derivative to the osteoarthritis-affected site. In some embodiments, the present method further comprises re-determining the levels of the at least one cartilage-degrading agent, the levels of the at least one cartilage-forming agent, or a pain score, or combinations thereof. In some embodiments, the present method further comprises modifying the second therapeutically effective amount.

In some embodiments, in addition to administering a therapeutically effective amount of a clostridial derivative to an OA-affected site, the present method further comprises administering corticosteroids and/or viscosupplements to the OA-affected site. Corticosteroids suitable for the present method includes methylprednisone acetate (DEPO-MEDROL), triamcinolone acetate (KENALOG 10, KENALOG 40), triamcinolone hexacetonide (ARISTOSPAN). Viscosupplements suitable for the present method include hyaluronate formulations, such as ADANT®, SYNOCROM® or SYNVISC®. The corticosteroids and/or viscosupplements can be administered concurrently, prior to and/or subsequent to the administration of the clostridial derivative. Viscosupplements administration to restore elastoviscosity of the joint (dosage, frequency, mode) can be carried out as well known to one of ordinary skill in the art.

The following non-limiting examples provide those of ordinary skill in the art with specific preferred methods to delay progression of osteoarthritis and/or repair cartilage defect, within the scope of the present disclosure, and it is not intended to limit the scope of the invention. In the following examples various modes of non-systemic administration of a botulinum neurotoxin can be carried out. For example, by intramuscular injection, non-intramuscular injection, intra-articular injection, extra-articular injection, peri-articular injection, subcutaneous injection or by implantation of a controlled release implant.

EXAMPLES

The following non-limiting examples provide those of ordinary skill in the art with specific preferred methods to treat conditions within the scope of embodiments of the present invention and are not intended to limit the scope of the invention.

Example 1—Botulinum Toxin Type A Therapy for Osteoarthritis (OA)

A double-blind, placebo controlled, randomized study was performed to evaluate the efficacy and safety of a single intra-articular (IA) injection of a botulinum toxin Type A (such as BOTOX®) compared with placebo as treatment for osteoarthritis (OA) knee pain. Participants were men or women aged 40 to 75 years (N=121).

Inclusion criteria include painful osteoarthritis in the study knee, able to walk without assistive walking devices, able to perform usual daily activities, and agree to maintain similar activity level throughout the study.

Exclusion criteria include:
Chronic pain conditions other than knee osteoarthritis,
Presence of bursitis, meniscus tear, ligament tear, or significant injury to the study knee within 1 year,
Surgery to the study knee within 24 weeks,
Treatment with hyaluronic acid in the study knee within 24 weeks,
Treatment with corticosteroids in the study knee within 12 weeks,
Diagnosis of myasthenia gravis, Eaton-Lambert syndrome, or amyotrophic lateral sclerosis,
Previous treatment with botulinum toxin of any serotype for any reason.

Study design: A single 200 U (2 mL) dose of a botulinum toxin Type A (BOTOX®) was injected into the intra-articular space of the study knee on Day 1. For the placebo comparator: a single 2 ml dose of normal saline was injected into the intra-articular space of the study knee on Day 1.

Primary outcome that was evaluated included change from Baseline in Daily Worst Pain Score. Secondary outcomes measures that were evaluated included change from baseline in in Western Ontario McMaster Arthritis Index (WOMAC™) Total Index Score; Change from Baseline in WOMAC Pain Score, Change from Baseline in WOMAC Physical Function Score and Change from Baseline in Patient Global Impression of Change Score.

Additionally, levels of specific biomarkers in the synovial fluid of patients before and after treatment were evaluated as described in Example 2.

Example 2: Effect of Botulinum Toxin Type A (BOTOX®) Treatment on Matrix-Metalloproteinase-1 (MMP-1) Level OA patients having a knee effusion were aspirated before botulinum toxin or placebo intra-articular injection to establish a baseline. The same patients were aspirated again by the end of the study (i.e., 12 weeks after botulinum toxin or placebo treatment) if knee effusion occurred. Knee effusion samples were collected into tubes pre-coated with protease inhibitors and then stored at −80° C. Pre- and post-treatment samples were analyzed with ELISA kits for each individual biomarker at the end of the study. The ELISA kits were commercially purchased and verified at the testing lab. Total protein for each sample was measured to normalize each biomarker. The relative change from baseline in each biomarker was assessed as below.

As shown in FIG. 1, the level of cartilage degrading-agent matrix metalloproteinase-1 (MMP-1) increased by more than 54% in the placebo-treated group (n=18), versus an increase of about 7.5% in the botulinum toxin treatment group (n=20).

Figure 2:
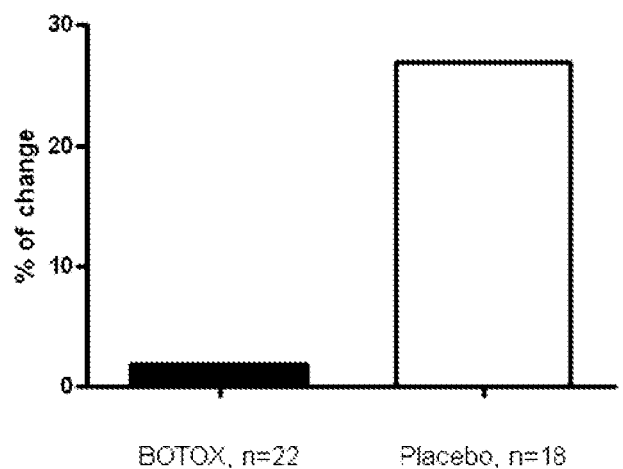
FIG. 2 shows the relative change from baseline over 12-week period in matrix metalloproteinase-3 (MMP-3) levels after treatment with an exemplary clostridial derivative or with a placebo in patients with primary knee osteoarthritis.

Example 3: Effect of Botulinum Toxin Type A (BOTOX®) Treatment on Matrix-Metalloproteinase-3 (MMP-3) Level As shown in FIG. 2, the level of cartilage degrading agent matrix metalloproteinase-3 (MMP-3), increased by 27% in placebo-treated group (n=18), versus less than 2% increase in the botulinum toxin treatment group (n=22).

These results show, among other things: (1) in the absence of effective treatments (placebo groups), progression of OA is manifested by a substantial increase in the levels of exemplary cartilage-degrading agents matrix-metalloproteinases 1 and 3 (MMP-1 and MMP-3, respectively); and (2) administration of botulinum toxin Type A (BOTOX®) significantly lessened the OA associated increase observed in the control or placebo group.

Figure 3:
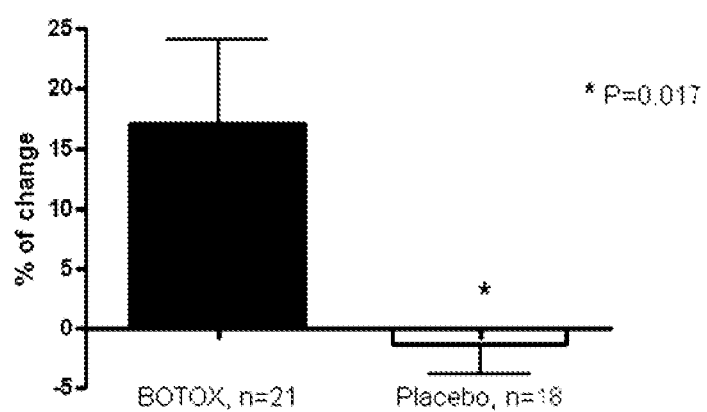
FIG. 3 shows the relative change from baseline over 12-week period in aggrecan levels after treatment with an exemplary clostridial derivative or a placebo in patients with primary knee osteoarthritis.

Example 4: Effect of Botulinum Toxin Type A (BOTOX®) Administration on Aggrecan Level As shown in FIG. 3, aggrecan level increased by 17% in the botulinum toxin treatment group (n=21), significantly higher than the placebo treatment group (−1.3%, n=18). In the context, this increase in synovial fluid flow indicates up regulation of aggrecan synthesis.

Figure 4:
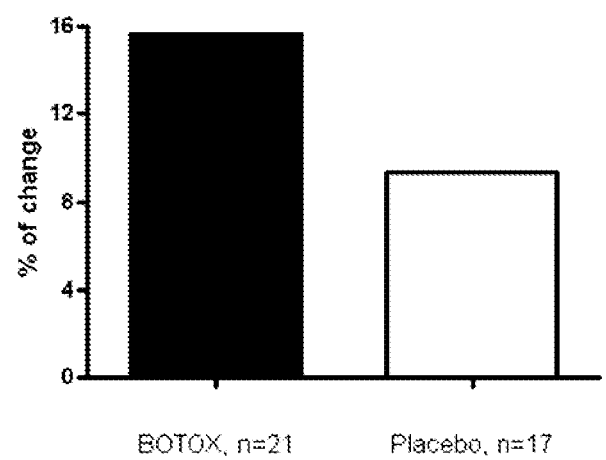
FIG. 4 shows the relative change from baseline over 12-week period in hyaluronic acid levels after treatment with an exemplary clostridial derivative or a placebo in patients with primary knee osteoarthritis.

Example 5: Effect of Botulinum Toxin Type A (BOTOX®) Administration on Hyaluronic Acid Level As shown in FIG. 4, the hyaluronic acid level increased by 15.9% in the botulinum toxin treatment group (n=21) versus 9.4% in the placebo group (n=17), respectively.

These results show, among other things: (1) in the absence of effective treatments (placebo groups), progression of OA is manifested by a small decrease in the levels of aggrecan and a small increase in the levels of hyaluronic acid; and (2) administration of a botulinum toxin Type A (BOTOX®) increased the aggrecan level significantly and amplified the increase in hyaluronic acid level moderately.

Example 6: Effect of Botulinum Toxin Type A (BOTOX®) Administration on Several Biomarkers in Individual Patients The effect of botulinum toxin treatment on a multitude of biomarkers, including inflammatory cytokine IL-6, matrix metalloproteinases MMP-1, MMP-3, MMP-9, cartilage-forming components aggrecan and hyaluronic acid, was evaluated for several individual patients. Table 1 lists the relative changes from baseline 12 weeks after botulinum toxin treatment, as described in Example 2.

TABLE 1

Relative Changes from baseline over 12-week period after Botulinum toxin treatment ("−" means reduction, "+" means increase)

| Patient ID | IL-6 (%) | MMP-1 (%) | MMP-3 (%) | Aggrecan (%) | HA (%) | Pain Score (0-10) |
|---|---|---|---|---|---|---|
| 1022 | −87 | −46 | −48 | +69 | +19 | −0.8 |
| 1072 | −66 | −77 | −73 | +15 | +26 | −5.4 |
| 1100 | −20 | −48 | −60 | +22 | +14 | −5.6 |
| 1121 | −86 | −17 | −30 | +15 | +48 | −3.7 |
| 1145 | +86 | −58 | −35 | +3 | ND | −2.3 |
| 1126 | +179 | −18 | −44 | — | — | −0.0 |
| 1148 | +154 | −26 | −28 | — | — | −3.1 |
| 1155 | +240 | −9.3 | −21 | — | — | Early termination |

Note:
the missing data in biomarkers were due to insufficient knee effusion volumes.

As shown in Table 1 and described in Examples 7 to 11, in some patients, botulinum toxin administration resulted in an increase in the levels of inflammatory cytokine IL-6, a decrease in the levels of MMP-1, MMP-3 or MMP-9; and an increase in the levels of aggrecan or HA. In other patients, botulinum toxin administration resulted in a reduction in the levels of inflammatory cytokine IL-6, a decrease in the levels of MMP-1, MMP-3 or MMP-9, and an increase in the levels of aggrecan or HA. These results suggest that the level changes in MMP-1, MMP-3, MMP-9, aggrecan or HA appear to occur independently of the level changes in IL-6.

Examples 7-14: Methods for Treating Osteoarthritis

Example 7

A 42 year old male, with a body weight of 86 kg and a height of 1.82 m, had been suffering from left knee pain for over 4 years. He was diagnosed with knee osteoarthritis, without any apparent knee trauma or surgery. Administrations of acetaminophen and NSAIDs failed to alleviate the pain, which severely limited his activities. X-ray rating showed that this patient's knee joint had Kellgren-Lawrence score of I (indicating formation of osteophytes on the tibial spines). He expressed his willingness to participate in a BOTOX knee osteoarthritis trial. His mean daily worst pain was 7.8 numerical rating scale (or NRS) for the 14-day period prior to treatment. He satisfied the inclusion and exclusion criteria for entering the trial. Ultrasound examination revealed knee effusion, which was withdrawn.

The patient was treated with 200 units of a botulinum toxin Type A (BOTOX®) by intra-articularly injection in the knee joint under ultra-sound guidance. Analysis of his post treatment knee effusion samples relative to the pretreatment samples showed a 20% decrease in the level of IL-6, a 48% and 60% decrease in the levels of MMP-1 and MMP-3, respectively, and an increase of 22% and 14% in the levels of aggrecan and hyaluronic acid, respectively.

The patient did not have any discomfort post injection. After one week, the patient reported that his knee pain via NRS was reduced from 7.8 to 6.3. His pain continued to improve, by the end of the 12 week study he rated his knee pain as 2.0 on the NRS; thus his total NRS pain reduction was 5.8. It has been established that a NRS improvement of at least 2.0 is clinical meaningful. He also reported that with the pain alleviated, he was able to resume his daily activities with much less limitation.

Example 8

A 47 year old female, with a body weight of 87 kg and a height of 1.6 m, had been suffering from left knee pain for over 4 years. She was diagnosed with idiopathic knee osteoarthritis. She had been treated with NSAIDs, intra-articular steroids or hyaluronic injections. However, these treatments failed to provide sufficient pain relief and functional improvement. She was willing to participate in the knee OA clinical trial. Her mean daily worst pain score was 5.9 NRS at baseline (the mean of 14-day pain scores). Her conditions satisfied the inclusion and exclusion criteria for the OA clinical trial. Ultrasound examination revealed knee effusion, which was withdrawn prior to treatment.

She was treated with about 200 units of a botulinum toxin Type A (BOTOX®) into the knee joint by intra-articular injection. No post injection discomfort was reported. Analysis of her post treatment knee effusion samples showed a decrease of 60% and 35% relative to the pretreatment samples in the levels of MMP-1, MMP-3, relatively and an increase of 86% in the level of IL-6.

After one week, the patient reported pain relief, her pain rating was 4.6 via NRS. After the 12 week study, her pain score was 3.6 via NRA by the end of the study with a total pain reduction of 2.3. It has been established that a NRS improvement of at least 2.0 is clinical meaningful.

Example 9

A 62 years old female with a body weight of 83 kg and a height of 1.69 m had been suffering from right knee pain for over 13 years. She was diagnosed with idiopathic knee Osteoarthritis. She was treated with NSAIDs for her knee pain. However, the prescribed pain killers upset her digestive system. She asked to participate in the knee OA clinical trial. Her baseline knee pain was 5.0 NRS 14 days prior to BOTOX intra-articular injection. She also satisfied other inclusion and exclusion criteria of the clinical trial. Ultrasound examination revealed knee effusion, which was withdrawn prior to treatment.

She was treated with 200 units of a botulinum toxin Type A (BOTOX®) into the knee joint by intra-articular injection. Analysis of her post treatment knee effusion samples relative to the pretreatment samples showed a decrease of 26% and 28% in the levels of MMP-1, MMP-3, respectively and an increase of 154% in the level of IL-6.

After one week, her pain reduced to 3.9. By the end of the 12 week study, her pain score reduced to 1.9 NRS with a total NRS pain reduction of 3.1. It has been established that a NRS improvement of at least 2.0 is clinical meaningful.

Example 10

A 63 year old male, with a body weight of 92 kg and a height of 1.78 m, was diagnosed with knee osteoarthritis. X-ray rating showed that this patient's knee joint had Kellgren-Lawrence score of I (indicating formation of osteophytes on the tibial spines). He expressed his willingness to participate in a BOTOX knee osteoarthritis trial. He satisfied the inclusion and exclusion criteria for entering the trial. Ultrasound examination revealed knee effusion, which was withdrawn.

The patient was treated with 200 units of a botulinum toxin Type A (BOTOX®) by intra-articularly injection in the knee joint under ultra-sound guidance. Analysis of his post treatment knee effusion samples relative to the pretreatment samples showed an 86% decrease in the level of IL-6, a 17%, 30% decrease in the levels of MMP-1 and MMP-3, respectively, and an increase of 15% and 48% in the levels of aggrecan and hyaluronic acid, respectively. The level of MMP-9 before treatment was 27 ng/ml. After botulinum toxin treatment, the level of MMP-9 was below quantitation limits, suggesting that the treatment resulted in a decrease in the level of MMP-9.

Example 11

A 67 years old female with a body weight of 76 kg and a height of 1.71 m was diagnosed with idiopathic knee Osteoarthritis. She asked to participate in the knee OA clinical trial and satisfied other inclusion and exclusion criteria of the clinical trial. Ultrasound examination revealed knee effusion, which was withdrawn prior to treatment.

She was treated with 200 units of a botulinum toxin Type A (BOTOX®) into the knee joint by intra-articular injection. Analysis of her post treatment knee effusion samples relative to the pretreatment samples showed a significant increase of almost 6 fold in the level of IL-6, an increase of 30% in the level of aggrecan and a decrease of 16% in the level of MMP-9.

Example 12

An active 34-year-old female who plays women ice hockey and is an avid weekend cyclist presents with right knee pain. Her physical therapist has used a variety of techniques including manipulation and stretches, which fail to resolve the pain. She takes simple anti-inflammatory medication to ease the pain; however they provide little relief. Her baseline NRS pain score is 7.0. She is treated with 250 μg of a TEM intra-articularly into the knee joint. After one week, the symptoms started to improve with significant improvement observed at week 12. Analysis of her post treatment knee effusion samples relative to the pretreatment samples shows an increase in the levels of aggrecan, hyaluronic acids, IL-1 and a decrease in the level of MMP-1, MMP-3. Furthermore, her post-treatment NRS pain scores are reduced by 5.0 points, with a post treatment score at week 12 of 2.0 NRS. It has been established that a NRS improvement of 2.0 is clinical meaningful.

Example 13

A 57 year old mechanic reports to his doctor that pain due to the arthritis in his $1^{st}$ carpometacarpal (CMC) joints of both hands and the base of the thumb joint cannot be flexed. The pain is becoming unbearable, and rates his pain at a 9 on the numerical rating scale (NRS) for pain at the doctor's office. Application of various topical creams that contain ingredients such as methyl salicylate, menthol and capsaicin are ineffective. The physician decides to administer a botulinum toxin type A in order to treat the arthritis.

Upon ultrasound inspection, it is observed that effusion accumulates in the right $1^{st}$ CMC joint, which was withdrawn and stored at −80° C. The doctor administers a total of 100 units of a botulinum toxin type A (BOTOX®) as follows: about 50 units into the right and left $1^{st}$ CMC joint cavity, respectively. After about 8 days, the patient reports that his arthritic pain is alleviated and ranks his pain at only a 2 on the same NRS. The arthritic pain remains alleviated for about at least about 3 months. There is no muscle weakness in his hands. He can use his hands for daily work now. However, there is effusion accumulation in the right $1^{st}$ CMC 3 months after the $1^{st}$ dosing, which was aspirated again and the levels of biomarkers in the effusion samples were assessed. It is found that IL-6 level increases from 20 pg/mL before treatment to 27 pg/mL post-treatment, MMP-1 level decreases from 120 ng/mL to 81 ng/mL, MMP-3 decreases from 450 ng/mL to 280 ng/mL, HA level increases from 2283 μg/mL to 2470 μg/mL and aggrecan level increases from 122 to 160 μg/mL. One year after treatment, the structure in both of the $1^{st}$ CMC joints of the hand have recovered to a normal range.

Example 14

A 39 year old female long distance runner (and known osteoarthritis sufferer) complains to her family doctor that her hip joints ache most of the time, and that her running regimen is being hampered by the pain, rating as an 8 on the doctor's NRS for pain. X-ray shows that her left hip joint space has moderate narrowing comparing with the right hip joint. She is diagnosed as hip osteoarthritis in both joints. After taking NSAIDs for 2 months, the patient reports that no improvement or alleviation of the pain. There is effusion in the left hip joint and aspiration is conducted under ultrasound guidance. The samples are stored at −80° C. Three months later, there is some re-accumulation of effusion in the left hip even though the pain is reduced. The doctor re-aspirates her effusion for further analysis. The pre- and post-treatment samples are analyzed with ELISA kits. The following changes are observed (from pre- to post-treatment): IL-6 level increases from 30 pg/mL to 39 pg/mL, MMP-1 level decreases from 131 ng/mL to 61 ng/mL, MMP-3 level decreases from 420 ng/ML to 260 ng/mL, HA level increases from 2163 μg/mL to 2590 μg/mL and aggrecan level increases from 112 to 169 μg/mL.

The doctor decides to treat the arthritis pain by administration of a botulinum toxin into hip joints. About 300 units of abobotulinumA (such as DYSPORT®) is bilaterally injected, i.e. about 150 units into the left and right hip cavity in 2 mL normal saline. After 10 days, the patient reports returns to the doctor's office for a follow up and reports that the pain in her hips is alleviated, and now when asked to rate her pain, she rates it as a 3, a good and desirable improvement. The patient is similarly administered the botulinum toxin every 6 months thereafter. She can now resume her running activity. Her left hip joint space recovers to the normal level as her right hip joint space after botulinum toxin treatments.

Many alterations and modifications may be made by those having ordinary skill in the art, without departing from the spirit and scope of the disclosure. Therefore, it must be understood that the described embodiments have been set forth only for the purposes of examples, and that the embodiments should not be taken as limiting the scope of the following claims. The following claims are, therefore, to be read to include not only the combination of elements which are literally set forth, but all equivalent elements for performing substantially the same function in substantially the same way to obtain substantially the same result. The claims are thus to be understood to include those that have been described above, those that are conceptually equivalent, and those that incorporate the ideas of the disclosure.

The invention claimed is:

1. A method for modifying the levels and/or activities of at least one agent associated with osteoarthritis-mediated cartilage degradation in a patient in need thereof, the method comprising locally administering a therapeutically effective amount of a botulinum toxin type A to an osteoarthritis-affected site of the patient, thereby mitigating the osteoarthritis-mediated cartilage degradation; wherein the administering is by intra-articular injection; wherein the therapeutically effective amount is greater than 300 units; and wherein the botulinum toxin type A is onabotulinumtoxinA.

2. The method of claim 1, wherein the administering alleviates the pain at the osteoarthritis-affected site of the patient.

3. The method of claim 1, wherein the administering reduces the levels and/or activities of at least one cartilage-degrading agent, increasing the levels and/or activities of at least one cartilage-forming component, or both.

4. The method of claim 1, wherein the therapeutically effective amount is from about 300 units to about 500 units.

5. The method of claim 1, wherein the at least one agent associated with osteoarthritis-mediated cartilage degradation comprises a cartilage-degrading agent, a cartilage-forming component, or mixtures thereof.

6. The method of claim 5, wherein the cartilage-degrading agent is a proteinase.

7. The method of claim 6, wherein the proteinase is selected from the group consisting of metalloproteinases, cysteine proteinases, aspartate proteinases, serine proteinases, and combinations thereof.

8. The method of claim 5, wherein the cartilage-forming component is selected from the group consisting of aggrecan, proteoglycans, collagens, hyaluronan, and combinations thereof.

9. The method of claim 1, wherein the osteoarthritis-affected site is selected from the group consisting of a knee joint, a hip joint, a hand joint, a shoulder joint, an ankle joint, a foot joint, an elbow joint, a wrist joint, a sacroiliac joint, a spine joint, and combinations thereof.

10. A method for alleviating osteoarthritis associated pain in a patient in need thereof, the method comprising locally administering a therapeutically effective amount of a botulinum toxin type A to an osteoarthritis-affected site of the patient; wherein the therapeutically effective amount is greater than 300 units; and wherein the botulinum toxin type A is onabotulinumtoxinA.

* * * * *